United States Patent
Bruewer et al.

(10) Patent No.: US 8,998,060 B2
(45) Date of Patent: Apr. 7, 2015

(54) RESISTIVE HEATED SURGICAL STAPLE CARTRIDGE WITH PHASE CHANGE SEALANT

(75) Inventors: Dean B. Bruewer, Fairfield, OH (US); Cory G. Kimball, Cincinnati, OH (US); Katherine J. Schmid, Cincinnati, OH (US); Brett E. Swensgard, West Chester, OH (US); William A. Daunch, Cary, NC (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 533 days.

(21) Appl. No.: 13/230,994

(22) Filed: Sep. 13, 2011

(65) Prior Publication Data

US 2013/0062393 A1 Mar. 14, 2013

(51) Int. Cl.
*A61B 17/04* (2006.01)
*A61B 17/00* (2006.01)
(Continued)

(52) U.S. Cl.
CPC . *A61B 17/07207* (2013.01); *A61B 2017/00893* (2013.01); *A61B 2017/00513* (2013.01); *A61B 2017/07271* (2013.01); *A61B 17/00491* (2013.01); *A61B 2017/00951* (2013.01); *A61B 2017/2927* (2013.01)

(58) Field of Classification Search
CPC .................... A61B 2017/00513; A61B 17/068; A61B 17/07207; A61B 17/07292; A61B 2017/07278; A61B 2017/07264; A61B 17/115; A61M 37/00
USPC ........... 227/175.1–180.1, 19, 176.1; 606/220, 606/219, 27; 604/115, 158, 219
See application file for complete search history.

(56) References Cited

U.S. PATENT DOCUMENTS

| 2,303,131 | A | 11/1942 | Morgan |
| 3,364,200 | A | 1/1968 | Ashton et al. |
| 3,496,940 | A | 2/1970 | Steinman |

(Continued)

FOREIGN PATENT DOCUMENTS

| CA | 481943 | 2/1947 |
| EP | 328 401 | 8/1989 |

(Continued)

OTHER PUBLICATIONS

Abstract for FR2789885.

(Continued)

*Primary Examiner* — Thanh Truong
*Assistant Examiner* — Joy N Sanders
(74) *Attorney, Agent, or Firm* — Frost Brown Todd LLC

(57) ABSTRACT

An apparatus for endosurgical use includes an instrument having an end effector and a staple cartridge insertable into the end effector. The staple cartridge includes staples, staple apertures, a resistive member, and a medical fluid. When coupled to a power source, the medical fluid is vaporized by the resistive member and expelled out the staple apertures onto the stapled tissue. The power source may be contained within the instrument. In one configuration, a resistive strip with strip contacts may electrically couple to a conductor in the end effector. The medical fluid may also be divided into a plurality of sealant pads corresponding to the staple apertures, and the medical fluid may be a depolymerizable cyanoacrylate, a sprayable thermoplastic urethane, or any vaporizable medicament or pharmaceutical. The staple drivers may include one or more apertures to permit the medical fluid to pass through or around the staple drivers.

20 Claims, 17 Drawing Sheets

(51) Int. Cl.
  *A61B 17/072* (2006.01)
  *A61B 17/29* (2006.01)

(56) References Cited

U.S. PATENT DOCUMENTS

| | | |
|---|---|---|
| 3,526,228 A | 9/1970 | Lyug |
| 4,222,383 A | 9/1980 | Schossow |
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,403,312 A * | 4/1995 | Yates et al. ........................ 606/50 |
| 5,411,193 A | 5/1995 | Culp |
| 5,415,334 A * | 5/1995 | Williamson et al. ....... 227/178.1 |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Shimizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,811 A * | 9/1998 | Yates et al. ........................ 606/50 |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,951,552 A * | 9/1999 | Long et al. ........................ 606/46 |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 * | 4/2007 | Heinrich et al. ........... 227/181.1 |
| 7,211,079 B2 | 5/2007 | Treat |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 * | 6/2008 | Shelton et al. ............. 227/175.1 |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,721,930 B2 | 5/2010 | McKenna et al. |
| 7,738,971 B2 | 6/2010 | Swayze et al. |
| 7,845,533 B2 | 12/2010 | Marczyk et al. |
| 8,062,330 B2 * | 11/2011 | Prommersberger et al. .. 606/215 |
| 2002/0165559 A1 | 11/2002 | Grant et al. |
| 2002/0165562 A1 * | 11/2002 | Grant et al. .................... 606/151 |
| 2003/0120284 A1 | 6/2003 | Palacios et al. |
| 2003/0183671 A1 | 10/2003 | Mooradian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0072827 A1 * | 4/2005 | Mollenauer ................. 227/180.1 |
| 2005/0101834 A1 | 5/2005 | Merade |
| 2005/0107810 A1 | 5/2005 | Morales et al. |
| 2005/0145671 A1 * | 7/2005 | Viola .......................... 227/175.1 |
| 2005/0154403 A1 | 7/2005 | Sauer et al. |
| 2005/0245965 A1 | 11/2005 | Orban, III et al. |
| 2005/0249772 A1 | 11/2005 | Maliviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0102453 A1 * | 5/2007 | Morgan et al. ................. 222/191 |
| 2007/0112360 A1 | 5/2007 | De Deyne et al. |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |

(56) References Cited

U.S. PATENT DOCUMENTS

| | | | |
|---|---|---|---|
| 2008/0078800 A1 | 4/2008 | Hess et al. | |
| 2008/0078801 A1 | 4/2008 | Shelton, IV et al. | |
| 2008/0078802 A1 | 4/2008 | Hess et al. | |
| 2008/0078803 A1 | 4/2008 | Shelton, IV et al. | |
| 2008/0078804 A1 | 4/2008 | Shelton, IV et al. | |
| 2008/0078805 A1 | 4/2008 | Omaits et al. | |
| 2008/0078806 A1 | 4/2008 | Omaits et al. | |
| 2008/0078807 A1 | 4/2008 | Hess et al. | |
| 2008/0081881 A1 | 4/2008 | Swetlin et al. | |
| 2008/0082124 A1 | 4/2008 | Hess et al. | |
| 2008/0082126 A1 | 4/2008 | Murray et al. | |
| 2008/0110959 A1 | 5/2008 | Orban, III et al. | |
| 2008/0114381 A1 | 5/2008 | Voegele et al. | |
| 2008/0114385 A1 | 5/2008 | Byrum et al. | |
| 2008/0114399 A1 | 5/2008 | Bonutti | |
| 2008/0125812 A1 | 5/2008 | Zubik et al. | |
| 2008/0128469 A1 | 6/2008 | Dalessandro et al. | |
| 2008/0140115 A1 | 6/2008 | Stopek | |
| 2008/0200949 A1 | 8/2008 | Hiles et al. | |
| 2008/0314960 A1 | 12/2008 | Marczyk et al. | |
| 2009/0001122 A1 | 1/2009 | Prommersberger et al. | |
| 2009/0076510 A1 | 3/2009 | Bell et al. | |
| 2009/0118747 A1 | 5/2009 | Bettuchi et al. | |
| 2009/0236388 A1* | 9/2009 | Cole et al. | 227/175.1 |
| 2010/0076429 A1* | 3/2010 | Heinrich | 606/49 |
| 2010/0181364 A1* | 7/2010 | Shelton et al. | 227/180.1 |
| 2010/0204641 A1* | 8/2010 | Wenchell | 604/22 |
| 2012/0012638 A1* | 1/2012 | Huang et al. | 227/176.1 |
| 2013/0032626 A1* | 2/2013 | Smith et al. | 227/176.1 |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 256 318 | 11/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2850281.
Abstract for JP1072740.
Abstract for JP11309151.
Abstract for JP3146773.
Abstract for JP5076586.
International Search Report dated Dec. 4, 2012 for Application No. PCT/US2012/054397.
International Search Report and Written Opinion dated Dec. 4, 2012 for Application No. PCT/US2012/054397.
International Preliminary Report on Patentability dated Mar. 18, 2014 for Application No. PCT/US2012/054397.

* cited by examiner

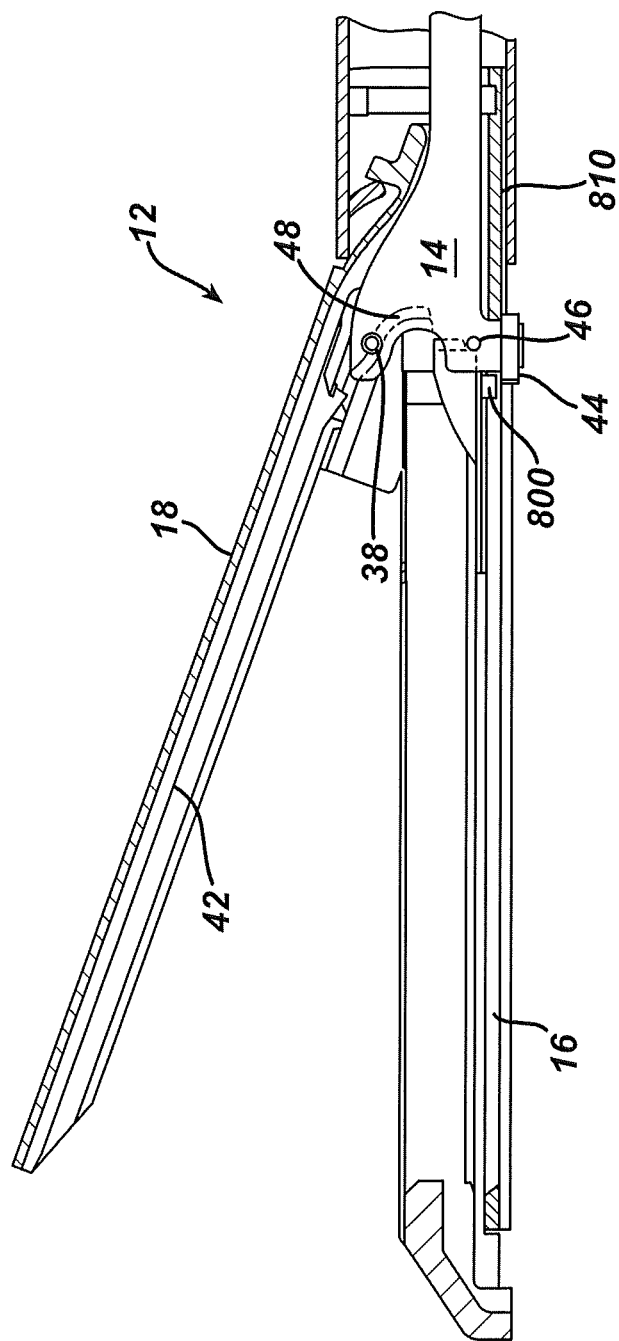

RESISTIVE HEATED SURGICAL STAPLE CARTRIDGE WITH PHASE CHANGE SEALANT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 16 depicts a partial side cross-sectional view of an end effector of FIG. 1A-1B.

Figure 1A:
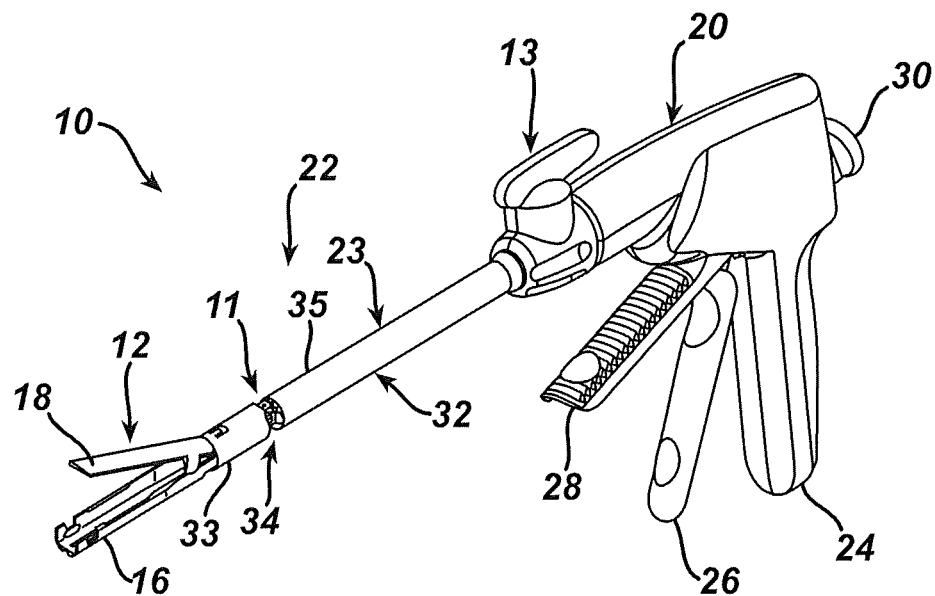
FIG. 1A depicts a perspective view of an articulating surgical instrument with an end effector in a nonarticulated position.
Figure 1B:
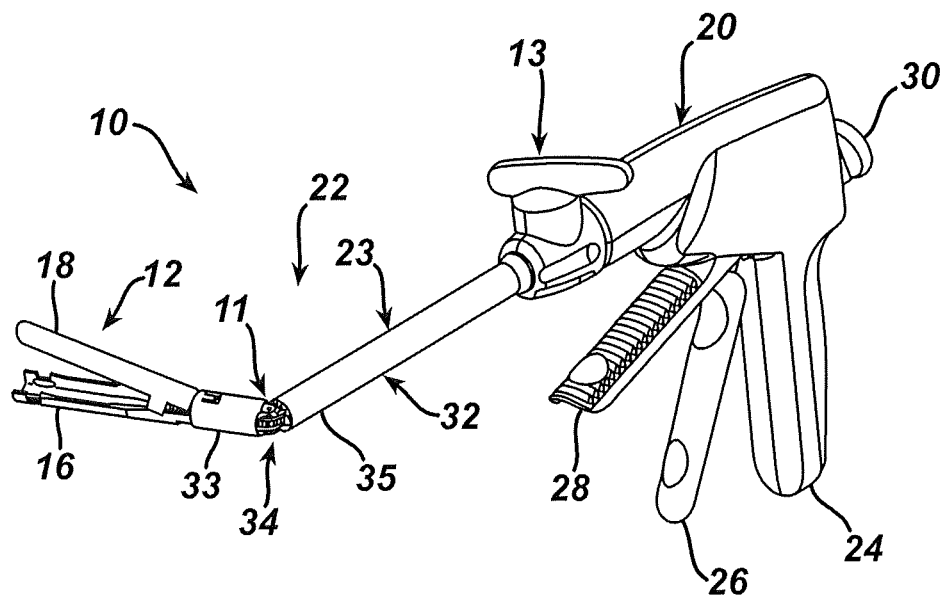
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
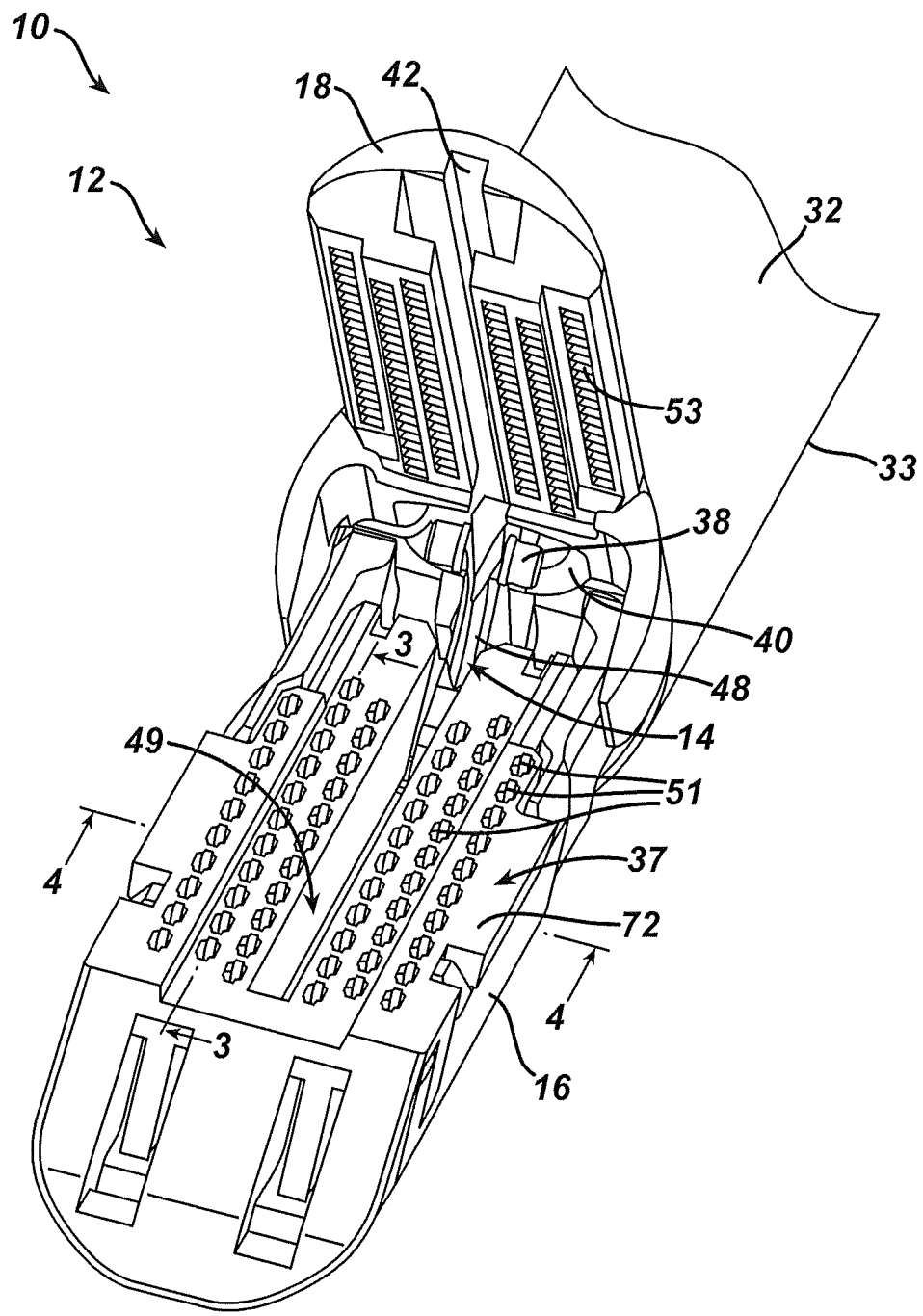
FIG. 2 depicts a perspective view of an opened end effector of the surgical instrument of FIGS. 1A-1B.
Figure 3A:
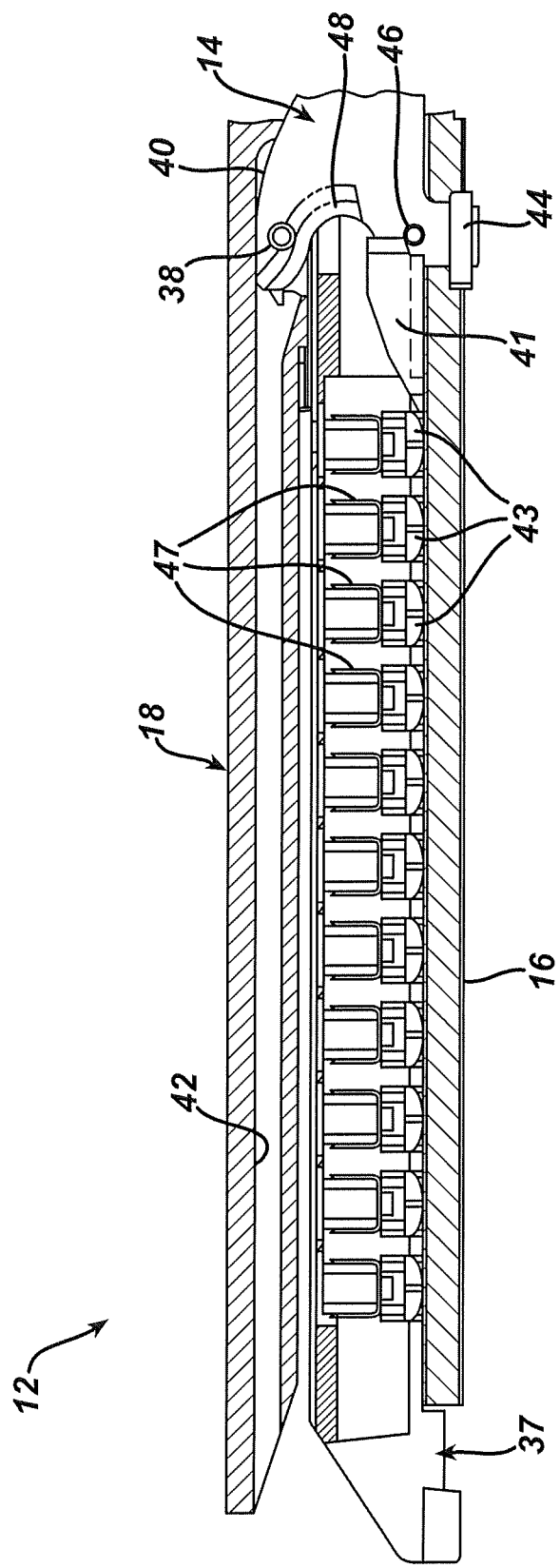
FIG. 3A depicts a side cross-sectional view of the end effector of FIG. 2, taken along line 3-3 of FIG. 2, with the firing bar in a proximal position.
Figure 3B:
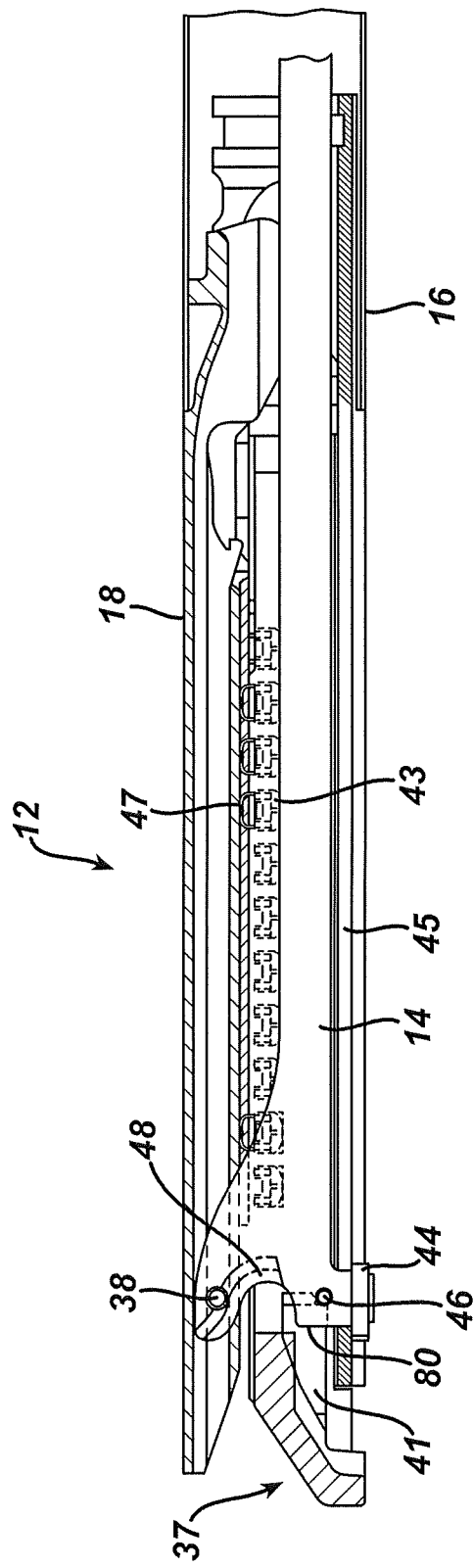
FIG. 3B depicts a side cross-sectional view of the end effector of FIG. 2, taken along line 3-3 of FIG. 2, but showing the firing bar in a distal position.
Figure 4:
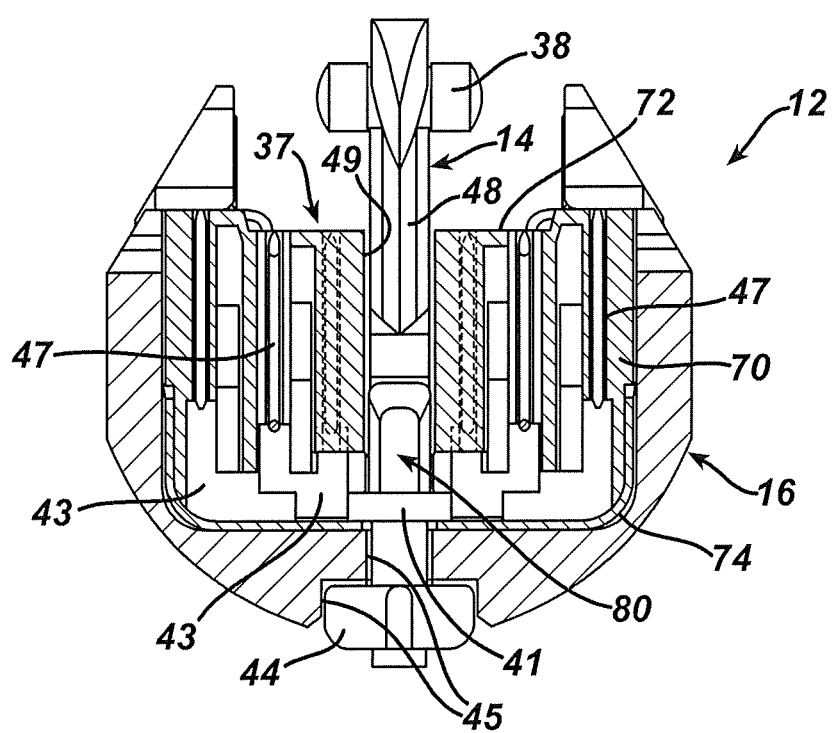
FIG. 4 depicts an end cross-sectional view of the end effector of FIG. 2, taken along line 4-4 of FIG. 2.
Figure 5:
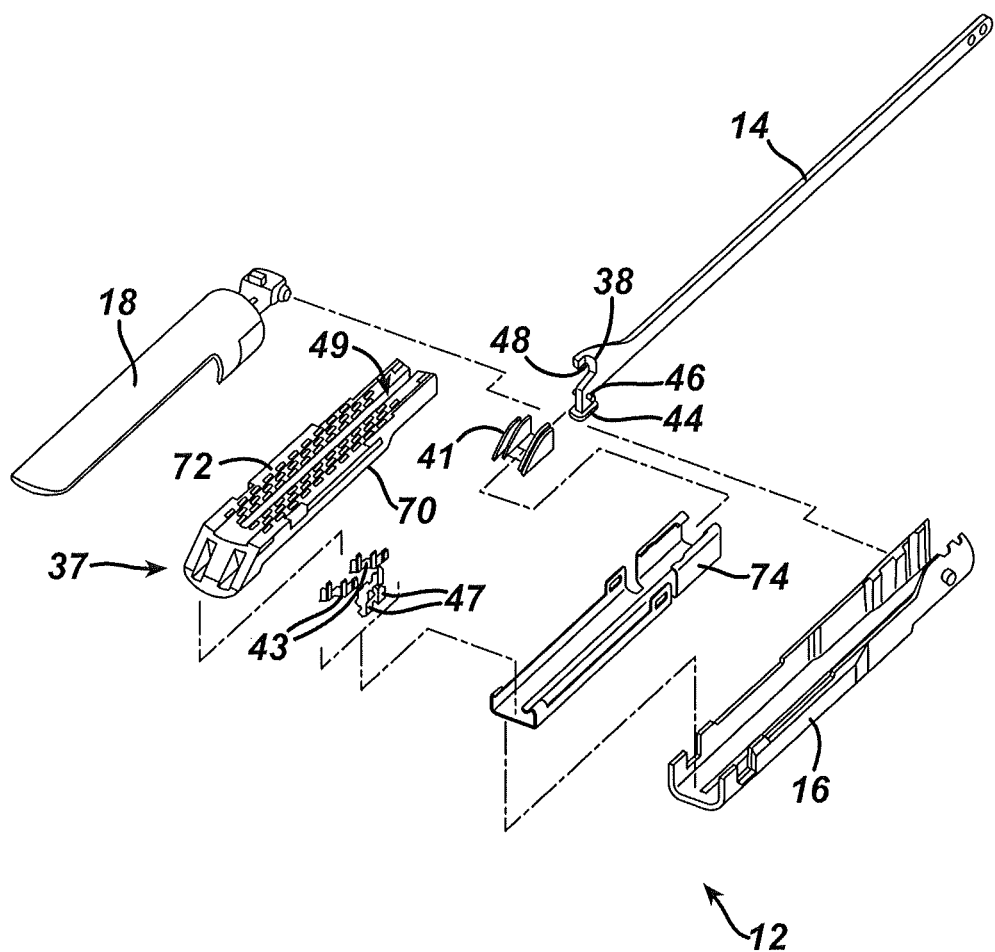
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
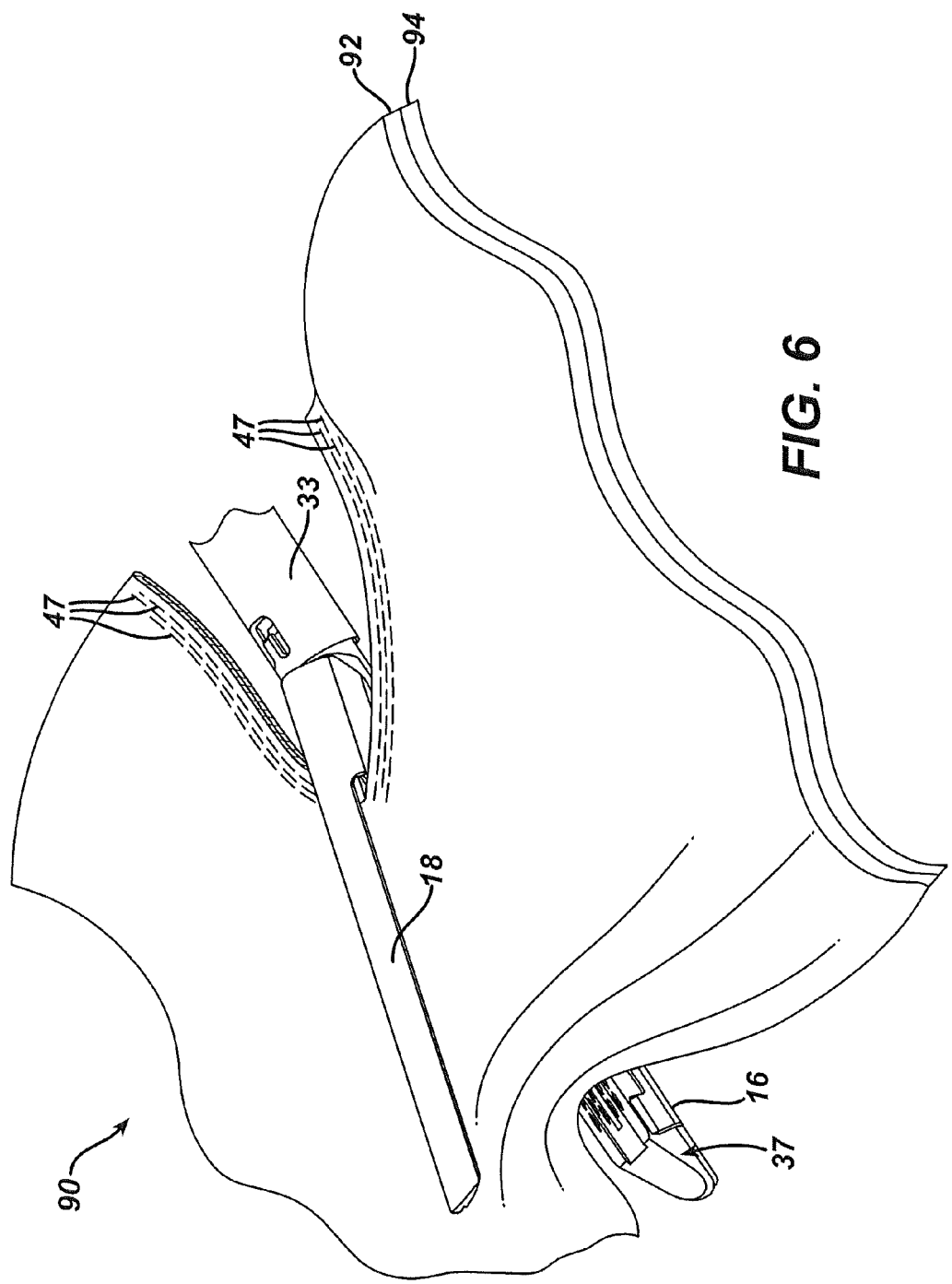
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Staple Cartridges

Figure 7:
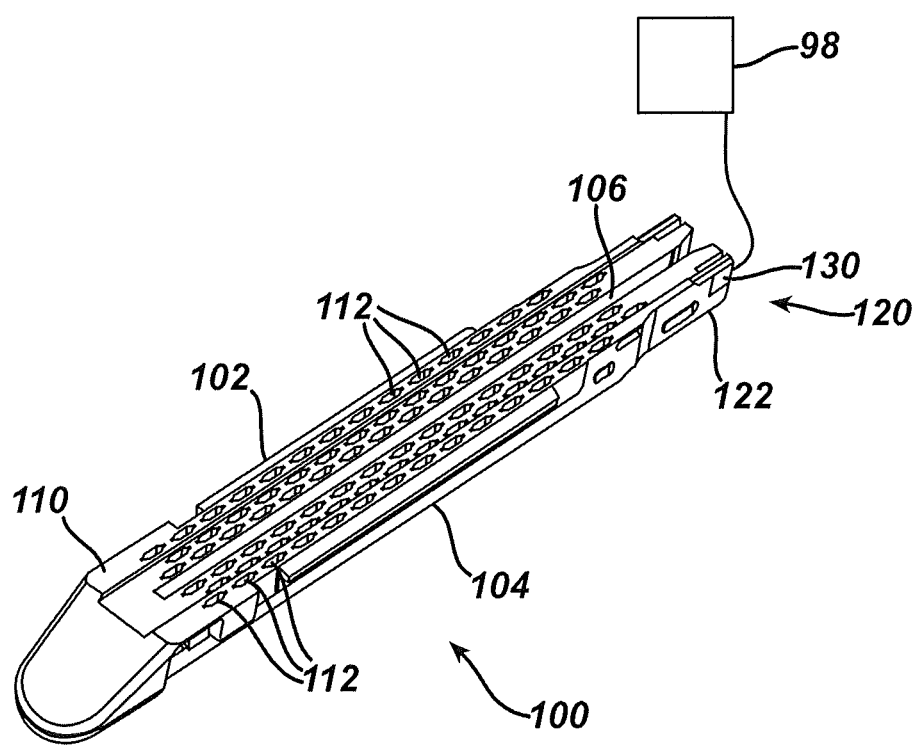
FIG. 7 depicts a perspective view of an exemplary staple cartridge.

FIG. 7 depicts an exemplary alternative staple cartridge (100) for use with instrument (10). Cartridge (100) comprises a cartridge body (102), a cartridge tray (104), a vertical slot (106), an upper deck (110), and a plurality of staple apertures (112) formed in upper deck (110). Vertical slot (106) extends longitudinally through cartridge body (102) and upper deck (110) such that firing bar (14) and cutting edge (48) pass through at least a portion of cartridge body (102). It should be understood that vertical slot (106) may longitudinally extend only partially through cartridge body (102) or along the entire length of cartridge body (102). Cartridge (100) of the present example has a proximal end (120) that includes a support portion (122). Support portion (122) further includes cartridge contacts (130) in this example, as will be described later herein, to electrically couple cartridge (100) with a power source (98) when cartridge (100) is inserted into end effector (12). As one of ordinary skill in the art will appreciate, cartridge contacts (130) are not limited to the proximal end (120) of cartridge (100). Indeed, cartridge contacts (130) may be located on the bottom surface of cartridge (100), such as on or through cartridge tray (104), or anywhere on cartridge body (102). Cartridge contacts (130) may alternatively be configured such that electrical power is communicated inductively, capacitively, and/or in any other suitable fashion. Furthermore, cartridge contacts (130) are merely optional.

Figure 8A:
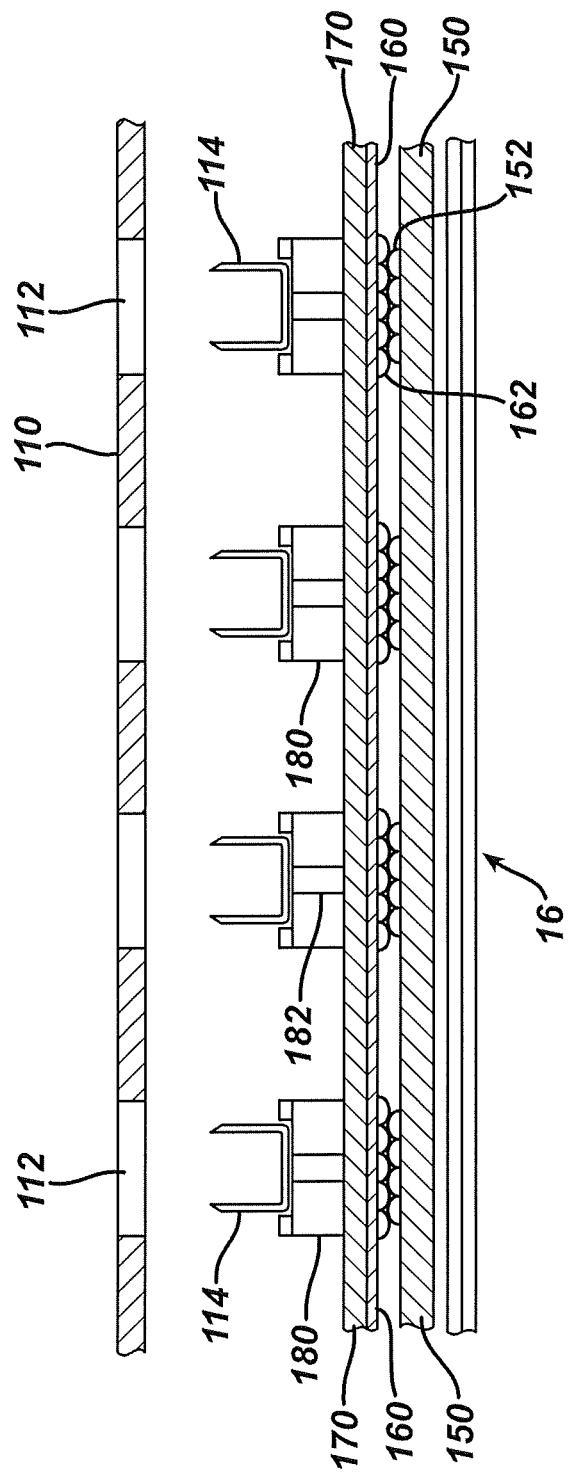
FIG. 8A depicts a partial side cross-sectional view of the cartridge of FIG. 7.

A. Exemplary Configuration and Operation of an Alternative Staple Cartridge having a Conductor and Resistive Strip FIGS. 8A-8D depict a sequential internal view of exemplary cartridge (100) when inserted into lower jaw (16) of end effector (12) and used to cut and staple tissue, such as tissue (90) of FIG. 6. Referring first to FIG. 8A, a plurality of staples (114), and staple drivers (180) are shown disposed within cartridge (100). In the present example, lower jaw (16) comprises a conductor (150) having a plurality of conductor contacts (152) extending from the top surface of conductor (150). Conductor (150) may comprise a metallic member having ridged contacts, a plastic member having an embedded metallic member and a plurality of contacts protruding from the plastic member, a printed circuit board (or PCB) with thin conductive channels and contacts (e.g., exposed traces, etc.), or any other suitable components and/or features to transmit electrical power to conductor contacts (152). Conductor contacts (152) are shown as a plurality of raised portions configured to electrically couple with a corresponding plurality of raised portions of strip contacts (162), though other suitable contact configurations will be apparent to one of ordinary skill in the art in view of the teachings herein. A thin resistive strip (160) having strip contacts (162) is coupled to cartridge body (102) such that when cartridge (100) is inserted into lower jaw (16), strip contacts (162) and conductor contacts (152) electrically couple. In one alternative, strip contacts (162) may extend through cartridge tray (104) or resistive strip (160) having strip contacts (162) may be integrated into cartridge tray (104). In another merely exemplary alternative, strip contacts (162) and conductor contacts (152) may be omitted and resistive strip (160) and conductor (150) may be a unitary piece, within cartridge tray (104), within cartridge body (102), or on lower jaw (16). As shown in the present example, the plurality of strip contacts (162) and conductor contacts (152) are each aligned with a respective staple aperture (112) such that when a charge is applied to conductor (150), resistive strip (160) heats a corresponding portion of resistive strip (160) below each staple aperture (112). As will be explained further below, alternative configurations for cartridge (100), conductor (150), and resistive strip (160) may be utilized.

A layer of sealant (170) is disposed above resistive strip (160). In the present example, sealant (170) is a substantially homogeneous continuum disposed within cartridge body (102). It should be understood that sealant (170) is not limited to sealants; rather, a variety of vaporizable items may be used without departing from the scope of the present disclosure. For instance, sealant (170) may comprise a depolymerizable cyanoacrylate, a sprayable thermoplastic urethane, a polyurethane prepolymer, medicaments, hemostatic agents, mucoadhesive polymers, poly vinylpyrrolidone (PVP), methyl cellulose (MC), sodium carboxy methylcellulose (SCMC), hydroxy propyl cellulose (HPC), and other cellulose derivatives, anionic hydrogels, cationic hydrogels, neutral hydrogels (such as carbapol, polyacrylates, chitosan or Eudragits), polyacrylic-polyethylene glycol copolymers (so-called buccal adhesives), thrombin, lyophilized thrombin (such as that used in Surgiflo® of Ethicon, Inc. in Somerville, N.J.), platelet poor plasma (PPP) platelet rich plasma (PRP), mussel-based or derived adhesives, calcium alginate, fibrin, adhesives, image enhancing agents, necrosing agents, sclerosing agents, coagulants, theraputic agents, analeptic agents, anesthesia agents, antidiuretic agents, analgesic agents, antiseptic agents, antispasmodic agents, cardiac agents, depressant agents, diuretic agents, hormonal agents, sedative agents, stimulant agents, vascular agents, time release agents, drugs, absorbable materials, colorants, plasticizing agents, bulking agents, tamponade materials, thixotropic agents, antibacterial agents, buffers, catalysts, fillers, micro particles, thickeners, solvents, natural or synthetic rubbers, stabilizers, pH modifiers, bioactive agents, cross-linking agents, chain transfer agents, fibrous reinforcements, colorants, preservatives, formaldehyde reducing or scavenging agents, and/or any other fluid, including liquids, gels, pastes, etc., or any other suitable medical fluid or hemostatic agent as will be apparent to one of ordinary skill in the art in view of the teachings herein.

Furthermore, sealant (170) may be impregnated with additional materials, such as various medicines (including pain killers or other suitable medicines), marking materials (such as radiopaque or echogenic markers and/or fluids), or any other suitable material that may be dispersed with sealant (170). Sealant (170) may further be a solidified material that may vaporize when subjected to thermal heating from resistive strip (160), or sealant (170) may be a liquid or semi-solid. If sealant (170) is a liquid or semi-solid, sealant may be contained within a reservoir or channel formed within resistive strip (160) or in an alternative structure located above resistive strip (160), such as a portion of cartridge body (102). One such alternative channel-type structure will be discussed below in reference to FIG. 11.

A plurality of staple drivers (180) are located above sealant (170). In the present example, staple drivers (180) each define a respective staple driver channel (182) formed through each staple driver (180) such that a vaporized material may pass through staple driver (180) once a staple (114) is ejected through staple aperture (112). Staple driver channel (182) may include an aperture formed through staple driver (180), such as driver aperture (510) shown in FIG. 13, or may include notches formed in one or more sides of staple driver (180), such as semi-circular notches (610) shown in FIG. 14, or other suitable configurations for staple driver channel (182). Staples (114) are located above staple drivers (180), and, in FIG. 8A, both staples (114) and staple drivers (180) are shown in an undeployed configuration. Staples (114) may further be detachably secured to staple drivers (180), such as through an adhesive, to ensure staples (114) remain aligned and atop staple drivers (180).

Figure 8D:
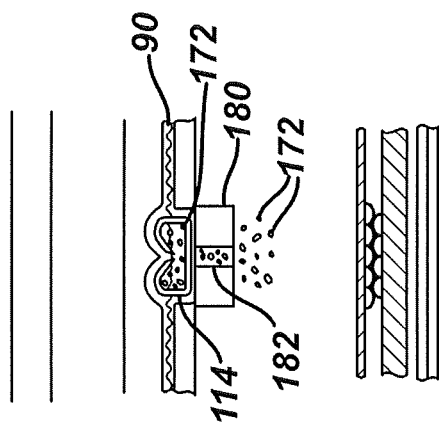
FIG. 8D depicts a portion of the side cross-sectional view of FIG. 8A showing the vaporized sealant being expelled through a staple driver channel.
Figure 8C:
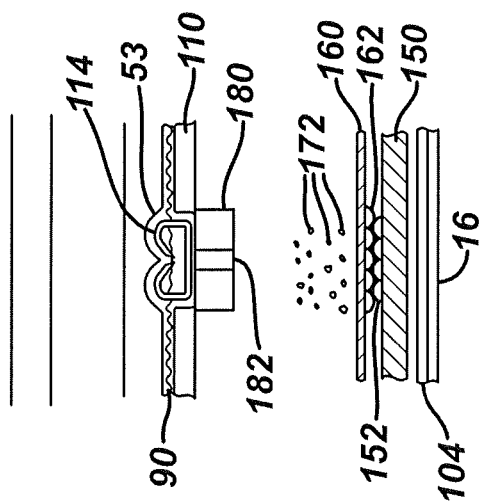
FIG. 8C depicts a portion of the side cross-sectional view of FIG. 8A showing a resistive strip vaporizing a sealant.
Figure 8B:
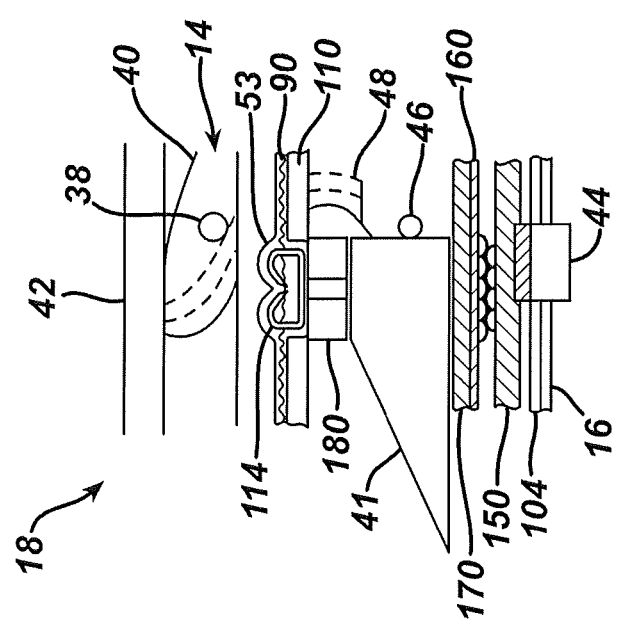
FIG. 8B depicts a portion of the side cross-sectional view of FIG. 8A showing a wedge sled vertically camming a staple driver.

Referring now to FIG. 8B, wedge sled (41) and firing bar (14) are shown driving staple (114) through tissue (90) while also severing tissue (90). As described above, anvil (18) compresses tissue (90) against upper deck (110) while staple driver (180) is cammed vertically by wedge sled (41) to drive staple (114) through tissue (90) and into staple forming pocket (53). While staple (114) is driven through tissue (90), conductor (150) and resistive strip (160) may remain inactive, though it should be understood that this is merely optional. Indeed, in one configuration, conductors (150) may be sequentially activated soon after cutting edge (48) severs tissue (90). For instance, wedge sled (41) and/or firing bar (14) may comprise a conducting portion that may electrically couple to conductor (150) and/or resistive strip (160) to provide power from power source (98). Alternatively, conductors (150) and/or resistive strip (160) and sealant (170) may be disposed on the side of staple driver (180) or elsewhere on the interior of cartridge body (102) as will be apparent to one of ordinary skill in the art in view of the teachings herein.

Referring back to the present example, as shown in FIG. 8C, while anvil (18) is still compressing tissue (90), power source (98) is activated and applied to conductor (150). Power source (98) may be activated through a toggle switch or button located on handle portion (20) of instrument (10) or through another control mechanism, including, but not limited to, a third trigger or an automated system receiving a signal from a sensor indicating the advancement of firing bar (14). Furthermore, power source (98) may be external to instrument (10) or power source (98) may be contained within instrument (10). One merely exemplary configuration for instrument (10) having an internal power source is disclosed by U.S. Pat. No. 7,738,971, entitled "Post-Sterilization Programming of Surgical Instruments," issued Jun. 15, 2010, the disclosure of which is incorporated by reference herein. Alternatively, power source (98) may be an external power source.

When power source (98) sends power to conductor (150), conductor (150) transfers the power to resistive strip (160) through conductor contacts (152) and strip contacts (162). Resistive strip (160) then heats appropriate portions of resistive strip (160) and portions of sealant (170) to vaporize sealant (170) into droplets (172). It should be understood that sealant (170) may be liquefied, atomized, or turned into any fluid and/or gaseous form such that sealant (170) may be expelled from cartridge (100). In the present example, the resistive heating vaporizes sealant (170) and produces a rapid pressure wave that expels sealant (170) from cartridge (100). Such resistive heating may further be accomplished in a substantially similar manner to thermal inkjets. Alternatively, droplets (172) may be formed through vibratory or pressure mechanisms, such as piezoelectric inkjet technology. As droplets (172) are formed, droplets (172) are expelled through a staple driver channel (182) and out staple aperture (112), as shown in FIG. 8D. In the present configuration, staple driver (180) is shown abutted against upper deck (110), though it should be understood that staple driver (180) may alternatively return to rest atop sealant (170) prior to vaporizing sealant (170). In an alternative configuration, a separate aperture may be provided through which droplets (172) may be expelled. After staple (114) has pierced tissue (90) and coupled thereto, droplets (172) of sealant (170) may settle on staple (114) and tissue (90). Droplets (172) then reconstitute on staple (114) and/or tissue (90). Such reconstitution may include repolymerization (such as for cyanoacrylate or polyacrylates), addition polymerization (such as for polyurethane prepolymer), and/or solidification from a liquid to a solid polymer. Once droplets (172) reconstitute, sealant (170) formed on staple (114) and tissue (90) may further aid in sealing tissue (90). A user of instrument (10) may delay releasing anvil (18) until a predetermined amount of time such that droplets (172) sufficiently reconstitute sealant (170) on tissue (90) and staple (114). As described above, a user may then change cartridges (100), and repeat the process to sever and seal additional portions of tissue (90).

Figure 9:
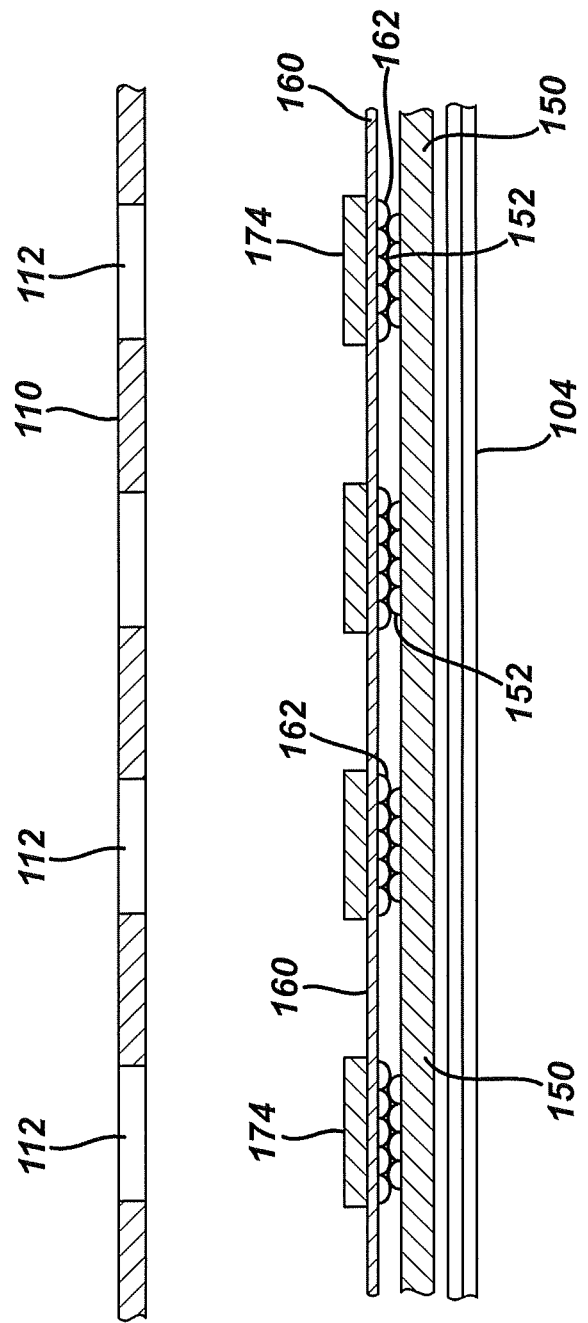
FIG. 9 depicts a partial side cross-sectional view of an exemplary alternative arrangement for a staple cartridge.

While one merely exemplary construction for cartridge (100) has been described, other suitable alternative constructions for cartridge (100) having a resistive heating portion will be apparent to one of ordinary skill in the art in view of the teachings herein. For instance, as shown in FIG. 9, an alternative arrangement for cartridge (100) shows sealant (170) divided into a plurality of individual sealant pads (174). Sealant pads (174) of the present example are aligned above strip contacts (162) and conductor contacts (152) and below staple apertures (112). Alternatively, conductor (150) having conductor contacts (152) may be located on or within cartridge tray (104) while resistive strip (160) and strip contacts (162) are located on or within cartridge body (102). Further still, a single strip contact (162) may be located on support portion (122) and a single conductor contact (152) may be located on a corresponding portion of lower jaw (16) instead of a plurality of contacts on cartridge (100) and lower jaw (16). In yet a further configuration, lower jaw (16) may comprise a resistive strip (160) coupled to power source (98) while cartridge tray (104) and/or cartridge body (102) comprise a plurality of apertures having sealant (170) contained therein. Thus, when cartridge (100) is coupled to lower jaw (16), the plurality of apertures having sealant (170) contained therein align with portions of resistive strip (160) in order to resistively heat sealant (170) when resistive strip (160) is coupled to power source (98). Furthermore, while the cartridges disclosed herein have been described in reference to a single-sided stapling cartridge, it should be understood that such cartridges may be modified to include dual-sided stapling cartridges.

B. Exemplary Alternative Resistive Assemblies

Figure 10:
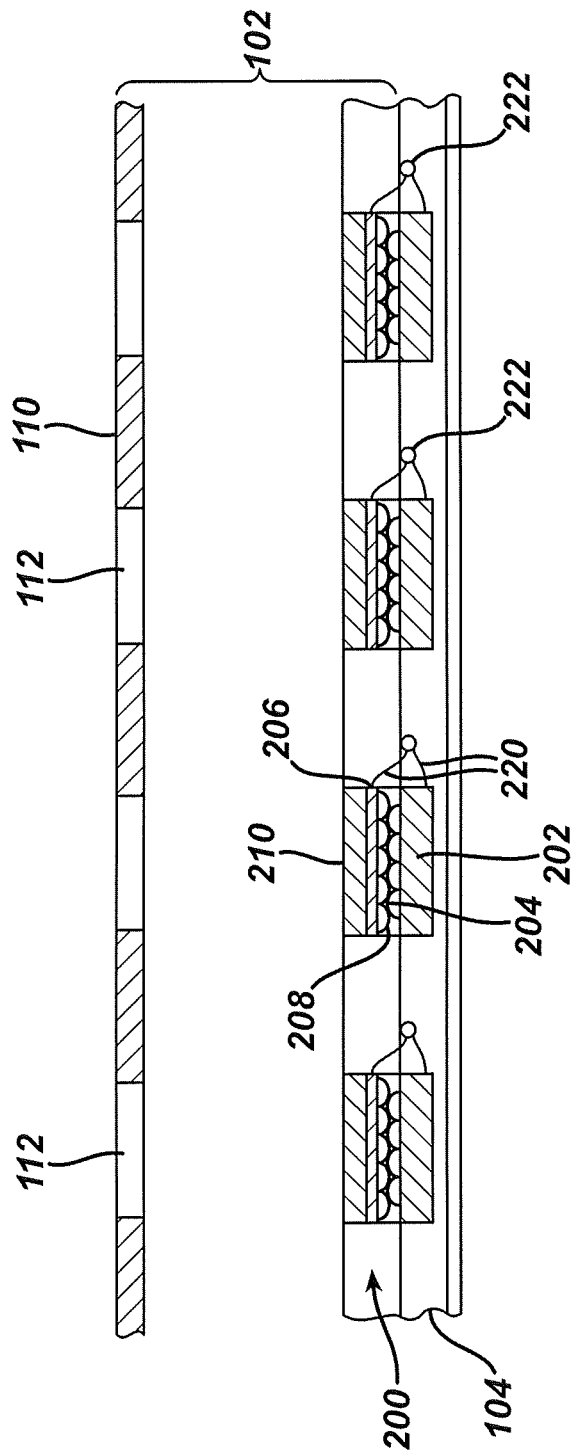
FIG. 10 depicts a partial side cross-sectional view of yet another exemplary arrangement for a staple cartridge.

In yet another configuration, shown in FIG. 10, a plurality of individual resistive assemblies (200) are arranged below each staple aperture (112) formed in upper deck (110). In this configuration, resistive assemblies (200) each comprise a conductor (202), a resistive strip (206), a sealant (210), a strip contact (208) and a conductor contact (204). Sealant (210) is not limited to a sealant, but may include any of the medical fluids and/or other items recited for sealant (170). As shown in the present example, conductors (202) having conductor contacts (204) are disposed within cartridge tray (104) while sealants (210) and resistive strips (206) having exposed strip contacts (208) are disposed within cartridge body (102). Thus, when cartridge body (102) is coupled to cartridge tray (104), strip contacts (208) electrically couple to conductor contacts (204). In one alternative configuration, conductors (202) may be embedded within lower jaw (14) while sealants (210) and resistive strips (206) are within cartridge body (102) and/or cartridge tray (104). Electrical leads (220) extend from conductors (202) and resistive strips (206) through one or more lead apertures (222) to electrically couple to power source (98), as described above. Electrical leads (220) may alternatively be integrated into the structure of lower jaw (16), cartridge tray (104), and/or cartridge body (102) in a similar manner to a PCB or in any other suitable manner as will be apparent to one of ordinary skill in the art in view of the teachings herein.

C. Exemplary Sealant Channels

Figure 11:
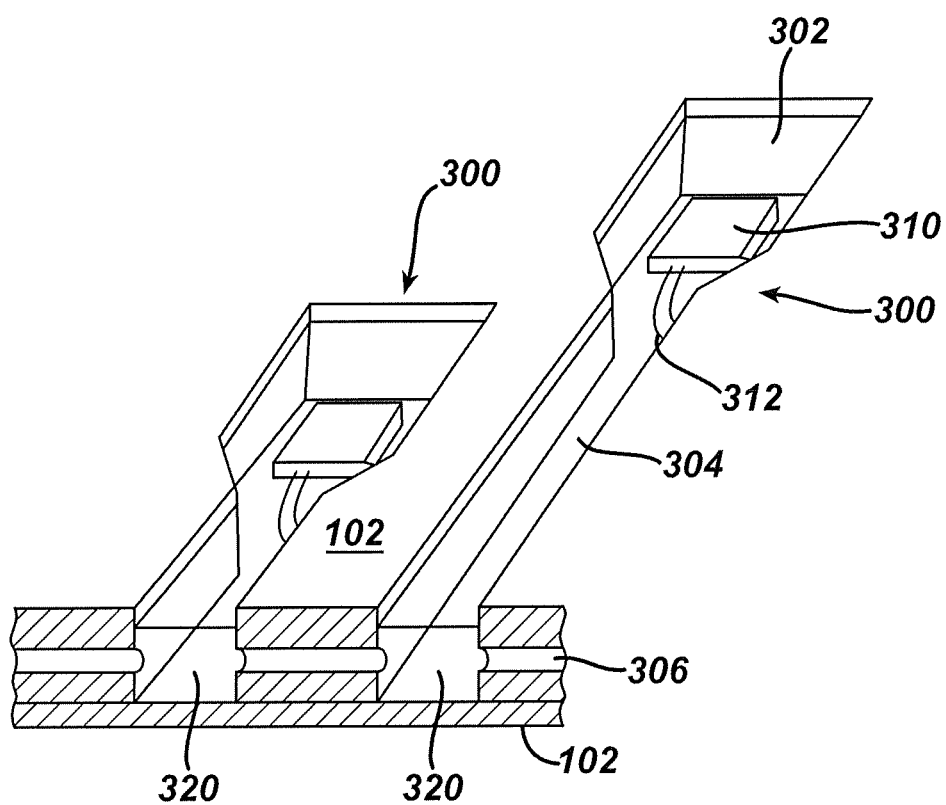
FIG. 11 depicts a partial perspective view of a pair of exemplary channels formed within a staple cartridge body.

Still a further configuration for a staple cartridge is presented in FIG. 11. A plurality of channels (300) are formed within cartridge body (102). Each channel (300) comprises a channel head (302) and a channel body (304). Channel bodies (304) may extend various distances such that each channel head (302) corresponds to a staple aperture, such as staple apertures (51, 112), when the staple apertures are distributed at different locations. For instance, in the exemplary cartridge (100) shown in FIG. 7, staple apertures (112) form three rows on either side of vertical slot (106) with staggered staple apertures (112). A plurality of channel bodies (304) of the present example are further configured to be in fluid communication with one or more other channel bodies (304) via ports (306). Ports (306) may be used to inject a sealant (320) into channels (300) during assembly to distribute sealant (320) throughout the plurality of channels (300) prior to sealant (320) solidifying, or, if a liquid or semi-solid sealant (320) is used, ports (306) may permit the plurality of channels (300) to draw from a common reservoir of sealant (320). Sealant (320) is not limited to a sealant, but may include any of the medical fluids and/or other items recited for sealant (170). It should be understood, however, that ports (306) are merely optional and channels (300) may be independent from each other, or a plurality of subsets of channels (300) may be connected by ports (306).

A resistive channel plate (310) is located within each channel head (302) such that resistive channel plate (310) may heat and vaporize sealant (320) below a corresponding staple aperture for ejection to the stapled tissue. Resistive channel plate (310) may be configured as an independent assembly, such as resistive assemblies (200), or resistive channel plate (310) may comprise only a resistive strip, such as resistive strip (160). If channel plate (310) comprises a resistive strip, one or more channel plate connectors (312) may be provided to electrically couple the resistive channel plates (310) to a conductor and/or power source. In the present configuration, plate connectors (312) are embedded within cartridge body to electrically couple to a single conductor, though it should be understood that channel plate connectors (312) may be configured in a variety of other manners as will be apparent to one of ordinary skill in the art in view of the teachings herein.

Figure 12:
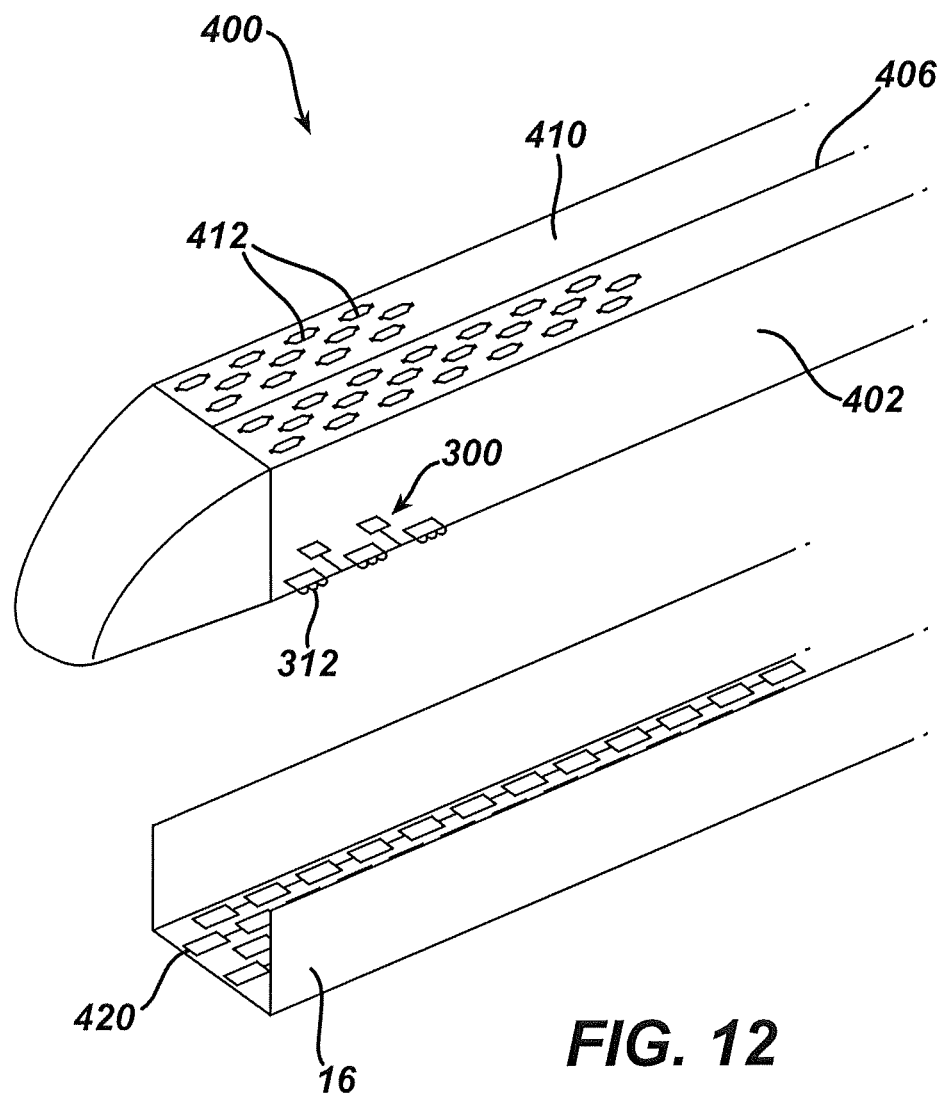
FIG. 12 depicts a partial perspective view of an exemplary staple cartridge having channels coupling to a lower jaw of the instrument of FIG. 1A-1B.

For instance, plate connectors (312) may be configured in a similar manner to strip conductors (162) of FIGS. 8A-8D, 9, and 10 and protrude out (or otherwise be exposed through) the bottom of cartridge body (102) and/or cartridge tray (104). One such configuration is shown in FIG. 12. Channels (300) having resistive plates (310) with plate connectors (312) are shown configured to be within a cartridge body (402) of a cartridge (400). Cartridge (400) is substantially similar in construction to cartridge (100) and cartridge (37), and cartridge (400) comprises a plurality of staple apertures (412), an upper deck (410), a cartridge body (402), and a vertical slot (406). Channels (300) are aligned with corresponding staple apertures (412). In the present example, lower jaw (16) comprises complementary end effector contacts (420) to electrically couple to plate connectors (312) when cartridge (400) is inserted into lower jaw (16). Alternatively, as noted with some of the above implementations, lower jaw (16) may comprise a single contact to electrically couple to a single contact on cartridge (400). In another alternative, lower jaw (16) may include a single conductor plate to electrically couple to plate connectors (312) or lower jaw (14) itself may have a portion that electrically couples to plate connectors (312).

While various configurations for channels (300) and cartridge (400) have been disclosed, other suitable configurations will be apparent to one of ordinary skill in the art in view of the teachings herein.

D. Exemplary Staple Drivers

Figure 13:
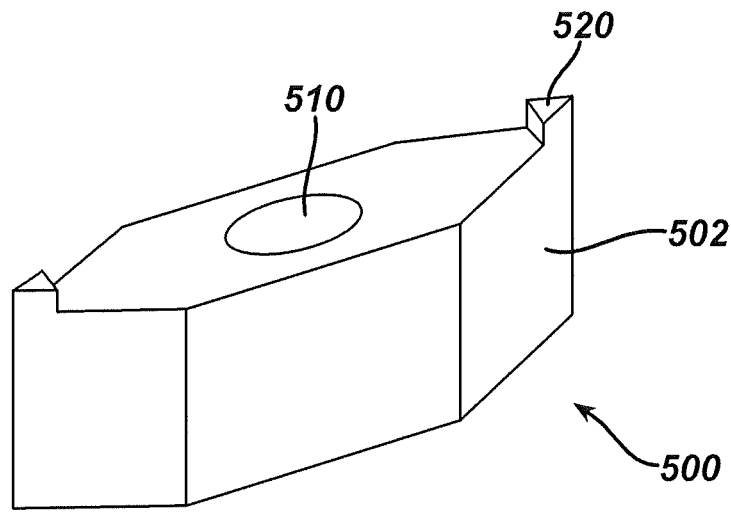
FIG. 13 depicts a perspective view of an exemplary staple driver having a staple driver aperture.
Figure 14:
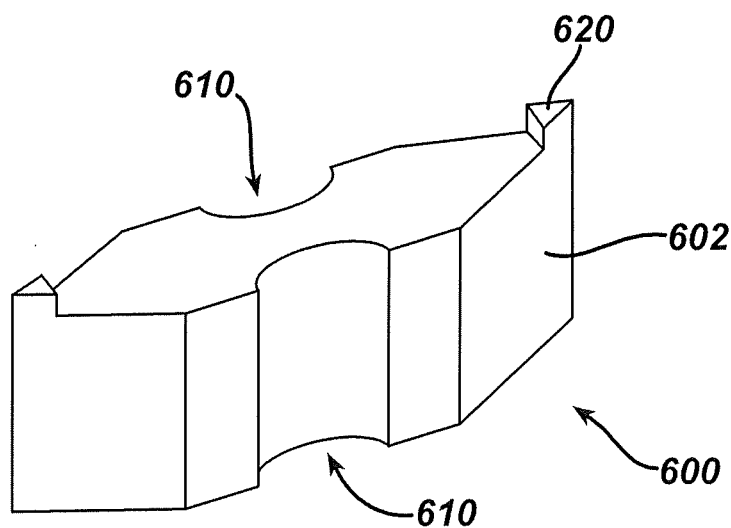
FIG. 14 depict a perspective view of an alternative exemplary staple driver having a pair of notches.

Referring now to FIGS. 13-14, different staple drivers may be utilized with the aforementioned configurations for expelling the vaporized sealants. FIG. 13 depicts a staple driver (500) having a staple driver body (502) with a driver aperture (510) formed therein and a pair of alignment tabs (520). Driver aperture (510) extends vertically through staple driver body (502) and is configured to permit the vaporized sealant to be expelled out through the staple apertures of a cartridge. Staple alignment tabs (520) extend vertically from staple driver body (520) and are configured to align a staple on staple driver (500) prior to deployment. Alignment tabs (520) may be further configured to detachably retain the staple, such as through an adhesive or a detachable mechanical connection. In yet a further configuration, alignment tabs (520) may be configured to couple to a receiving notch (not shown) formed within an upper deck of a cartridge, such as upper deck (110), such that staple driver (500) couples to and remains abutted against the upper deck, even when firing bar (14) is retracted. In such a configuration, any of the foregoing configurations may then be activated to expel a sealant through driver aperture (510). An alternative staple driver (600) is depicted in FIG. 14. Alternative staple driver (600) is substantially similar in configuration to staple driver (500), except staple driver (600) comprises a pair of semi-circular notches (610) formed on the sides of staple driver body (602) to permit a sealant to pass through the notches and past staple driver (600). Of course, as with other components described herein, other suitable configurations for staple drivers (500, 600) will be apparent to one of ordinary skill in the art in view of the teachings herein.

Figure 15:
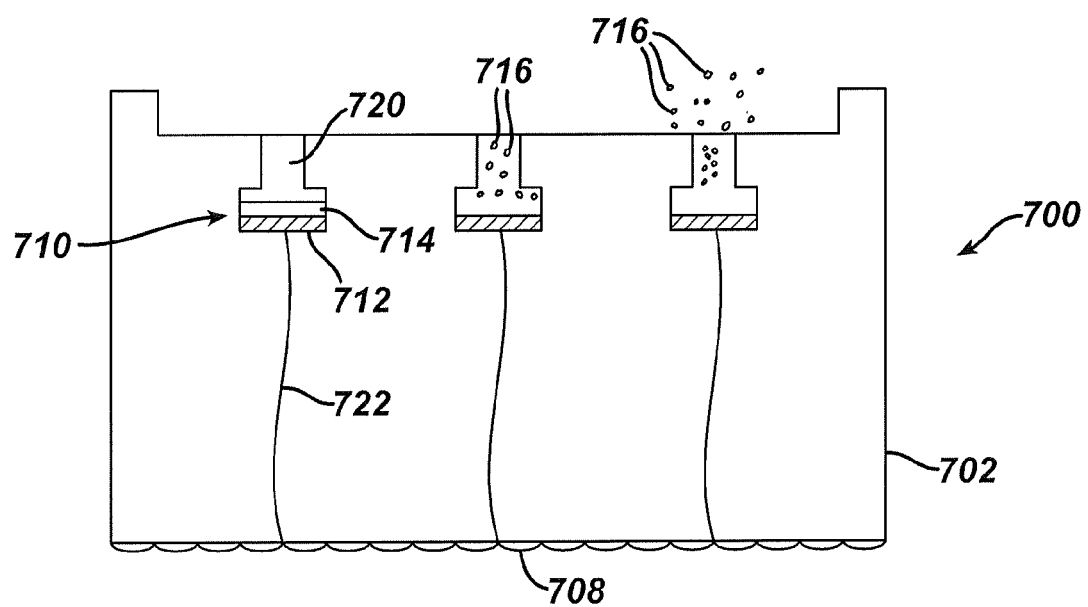
FIG. 15 depicts a side cross-sectional view of yet another exemplary staple driver having a plurality of integrated resistive strips and sealants.

In yet a further configuration shown in FIG. 15, one or more resistive strips (712) and sealants (714) are embedded within a corresponding chamber (710) in staple driver (700) or coupled to staple driver body (702) of staple driver (700). Sealant (714) is not limited to a sealant, but may include any of the medical fluids and/or other items recited for sealant (170). In this configuration, staple driver (700) has a plurality of staple driver contacts (708) on the bottom surface of staple driver (700), though it should be understood that staple driver contacts (708) may be located anywhere on staple driver (700). A connector (722) electrically couples driver contacts (708) to resistive strips (712), though it should be understood that this is merely optional, and resistive strips (712) may be integrally coupled to driver contacts (708). One or more apertures (720) formed within staple driver body (702) are configured to permit the expulsion of the vaporized sealant (716) to seal the staple and tissue. In the present configuration, driver contacts (708) are configured to electrically couple to one or more contacts located on firing bar (14) and/or wedge sled (41). When firing bar (14) is fully extended (and therefore the staples from the cartridge have been expelled out from the staple apertures), power source (98) may applied to the one or more contacts on firing bar (14), thereby triggering resistive strips (712) to vaporize sealant (714) to be expelled out through apertures (720). Alternatively, if wedge sled (41) comprises contacts, or if wedge sled (41) comprises conductive material, power source (98) may be coupled to wedge sled (41) while wedge sled (41) cams staple driver (700) vertically. As will be appreciated, this may vaporize sealants (714) while the staples are being driven through the tissue. This may reduce the time needed for sealant (714) to reconstitute to seal the staples and tissue. In yet a further configuration, driver contacts (708) may be on one or more sides of staple driver body (702) to electrically couple to corresponding contacts on the sidewall of the pocket through which staple driver (700) moves.

While various configurations for staple drivers (500, 600, 700) have been disclosed, other suitable configurations will be apparent to one of ordinary skill in the art in view of the teachings herein.

E. Exemplary Configuration for End Effector Electrical Coupling

FIG. 16 shows an end effector (12) having one or more electrical contacts (800) coupled to a remote power source, such as power source (98), via connector (810). As noted previously, power source (98) may be located within handle portion (20) (shown in FIG. 1A-1B), or power source (98) may be external to instrument (10). Electrical contact (800) in the present arrangement couples to a corresponding cartridge contact, such as cartridge contacts (130) of cartridge (100), when a cartridge is inserted into lower jaw (16). Electrical contact (800) may be configured to be used multiple times with multiple staple cartridges during the use of instrument (10). While only a single electrical contact (800) is depicted, it should be understood that more than one electrical contact (800) may be utilized. Indeed, it may be useful to provide redundant electrical contacts (800) for instances where blood or other bodily fluids may interfere with the electrical connection of one or more of electrical contacts (800), though it should be understood that this redundancy is merely optional. Furthermore, while electrical contact (800) is shown located near the proximal end of lower jaw (16), other suitable locations for electrical contact (800) on lower jaw (16), anvil (18), or firing bar (14) will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
   (a) an instrument comprising:
      (i) a handle portion,
      (ii) an end effector comprising:
         (1) a lower jaw,
         (2) a pivotable anvil; and
   (b) a staple cartridge insertable into the end effector, the staple cartridge comprising:
      (i) a cartridge body having an upper deck, the upper deck comprising:
         (1) a vertical slot formed in the upper deck and extending longitudinally from a proximal end of the upper deck, wherein a cutting edge is translatable longitudinally through the vertical slot, and
         (2) a plurality of staple apertures,
      (ii) one or more staple drivers vertically translatable relative to the cartridge body, wherein each staple driver includes a driver channel configured to provide a pathway for fluid communication,
      (iii) a plurality of staples disposed above the one or more staple drivers, wherein the plurality of staples are vertically translatable relative to the cartridge body,
      (iv) a resistive member disposed within the cartridge body,
      (v) a medical fluid having at least a portion in communication with the resistive member, wherein the resistive member is operable to provide communication of the medical fluid through the driver channels of the one or more staple drivers.

2. The apparatus of claim 1 wherein the resistive member comprises a resistive strip.

3. The apparatus of claim 2 wherein the lower jaw comprises a conductor, wherein the conductor is selectively coupled to a power source.

4. The apparatus of claim 3 wherein the resistive strip comprises strip contacts, wherein the conductor comprises conductor contacts, wherein the strip contacts are operable to electrically couple to the conductor contacts.

5. The apparatus of claim 4 wherein at least a portion of the strip contacts is in substantial vertical alignment with the plurality of staple apertures.

6. The apparatus of claim 1 wherein the medical fluid comprises a plurality of sealant pads.

7. The apparatus of claim 6 wherein at least a portion of each of the sealant pads is in substantial vertical alignment with the plurality of staple apertures.

8. The apparatus of claim 1 wherein each driver channel comprises an aperture extending vertically through the one or more staple drivers.

9. The apparatus of claim 1 wherein each driver channel comprises a notch extending vertically on a side of the one or more staple drivers.

10. The apparatus of claim 1 wherein the medical fluid comprises a depolymerizable cyanoacrylate or a sprayable thermoplastic urethane.

11. The apparatus of claim 1 wherein the medical fluid is a vaporizable medicament or pharmaceutical.

12. The apparatus of claim 1 wherein the cartridge body comprises a cartridge channel formed in a base portion of the cartridge body, wherein the resistive member and the medical fluid are disposed within the cartridge channel.

13. The apparatus of claim 1 further comprising a contact coupled to the resistive member and operable to electrically couple the resistive member to a power source.

14. The apparatus of claim 13 wherein the cartridge body comprises a proximal end having a support portion and wherein the contact is located on the support portion.

15. The apparatus of claim 13 wherein the power source is contained within the instrument.

16. An apparatus for endosurgical use, the apparatus comprising:
   (a) a cartridge body having an upper deck, the upper deck comprising:
      (i) a vertical slot formed in the upper deck and extending longitudinally from a proximal end of the upper deck, and
      (ii) a plurality of staple apertures;
   (b) one or more staple drivers vertically translatable relative to the cartridge body;
   (c) a plurality of staples, wherein the plurality of staples are vertically translatable relative to the cartridge body;
   (d) a plurality of resistive members disposed within the cartridge body;
   (e) a medical fluid having at least a portion disposed between the plurality of resistive members and the one or more staple drivers; and
   (f) a contact coupled to the plurality of resistive members and operable to electrically couple the plurality of resistive members to a power source.

17. The apparatus of claim 16 further comprising a plurality of channels formed in the cartridge body, wherein the plurality of resistive members are disposed within the plurality of channels.

18. The apparatus of claim 17 further comprising a port, wherein the port is configured to provide fluid communication between two or more of the plurality of channels.

19. The apparatus of claim 17 wherein at least a portion of the medical fluid is contained within a reservoir in fluid communication with one or more channels of the plurality of channels.

20. An apparatus comprising:
   (a) an instrument comprising:
      (i) a body portion,
      (ii) an end effector, wherein the end effector is distal to the body, the end effector comprising:

(1) a first member, and
(2) a second member, wherein the first member is movable relative to the second member; and (b) a staple cartridge insertable into the second member, the staple cartridge comprising:
(i) a cartridge body,
(ii) a plurality of staples,
(iii) a plurality of staple drivers operable to drive the plurality of staples from the cartridge body, and
(iv) a fluid communication assembly operable to drive fluid through the staple drivers to tissue captured between the first and second member.

\* \* \* \* \*